United States Patent [19]
Pressesky

[11] Patent Number: 5,898,499
[45] Date of Patent: Apr. 27, 1999

[54] METHOD AND APPARATUS FOR DETECTING SURFACE DISCONTINUITIES BASED ON CHANGES IN AN OPTICAL PATH LENGTH DURING BEAM SCANNING

[75] Inventor: Jason L. Pressesky, Menlo Park, Calif.

[73] Assignee: Seagate Technology, Inc., Scotts Valley, Calif.

[21] Appl. No.: 08/792,172

[22] Filed: Jan. 30, 1997

Related U.S. Application Data

[60] Provisional application No. 60/010,819, Jan. 30, 1996.

[51] Int. Cl.$^6$ ..................................................... G01B 9/02
[52] U.S. Cl. ........................................ 356/357; 356/237.2
[58] Field of Search .................................... 356/349, 351, 356/357, 358, 237; 250/559.44, 559.45, 559.48

[56] References Cited

U.S. PATENT DOCUMENTS

| | | | |
|---|---|---|---|
| 4,832,487 | 5/1989 | Mikuaiya et al. | 356/237 |
| 4,844,616 | 7/1989 | Kulkarni et al. | 356/237 |
| 5,389,794 | 2/1995 | Allen et al. | 356/237 |
| 5,661,559 | 8/1997 | Baezoczky et al. | 356/353 |

OTHER PUBLICATIONS

"The Gaussian Beam", Fundamentals of Photonics, Saleh, et al, pp. 81–87, 1991.

*Primary Examiner*—Samuel A. Turner
*Attorney, Agent, or Firm*—Frederick W. Niebuhr

[57] ABSTRACT

A system is disclosed for detecting local surface discontinuities in magnetic data storage disks. The system includes a spindle that rotatably supports a magnetic disk being tested. An interferometer generates a laser beam which is guided through an optics assembly supported above the magnetic disk, for linear movement radially of the disk. The combined radial and linear movement causes the laser beam to trace a spiral scanning path on the disk surface. The disk surface scatters the laser energy, a portion of which is returned to the interferometer and caused to interfere with a reference beam. The resulting interference intensity fluctuates in response to changes in the optical path length, thus measuring topographies of the discontinuities. A discontinuity recognition triggering pulse can be positioned in time with respect to indexing pulses, to identify the location of the associated discontinuity radially and angularly of the disk. The triggering pulses limit the storage of scanned surface data to the part of the data that locates and characterizes discontinuities exceeding a predetermined size threshold.

34 Claims, 4 Drawing Sheets

METHOD AND APPARATUS FOR DETECTING SURFACE DISCONTINUITIES BASED ON CHANGES IN AN OPTICAL PATH LENGTH DURING BEAM SCANNING

This application claims the benefit of Provisional Application Ser. No. 60/010,819 entitled "Scanning Laser Interferometer for Disk Evaluation (SLIDE)", filed Jan. 30, 1996.

BACKGROUND OF THE INVENTION

The present invention relates to the fabrication of data storage media, and more particularly to processes and devices for accurately characterizing the surfaces of rigid disk media.

Disk drives typically employ one or more rotatable disks in combination with transducers supported for generally radial movement relative to the disks. Each transducer is maintained spaced apart from its associated disk, at a "flying height" governed by an air bearing caused by disk rotation. Present day transducer flying heights typically range from about 25 nm to about 50 nm, and experience velocities (relative to the disk, due to disk rotation) in the range of 5–15 m/sec. Effective recording and reading of data depend in part upon maintaining the desired transducer/disk spacing. Flaws or discontinuities in an otherwise planar disk surface can interfere with reading and recording, and present a risk of damage to the transducer, the disk recording surface, or both. The continuing increase in data recording density in disk drives leads to more stringent requirements as to disk surface planarity, requiring improved manufacturing techniques to ensure that the number and size distribution of flaws or discontinuities remain below increasingly strict thresholds.

A critical aspect of rigid disk media manufacturing is the quality of substrates, upon which various magnetic thin films are to be deposited. Flaws in the substrate surface tend to be replicated by subsequent thin film layers, to become flaws in the finished product. Performance testing, i.e. in a disk drive or other typical usage environment, is not possible until after thin film layers have been applied to the substrate to provide the desired transducer flying height and glide characteristics. Destructive testing is unsatisfactory, and any visual inspection is difficult, because of the need to recognize potentially damaging flaws in the two micrometer range.

Therefore, it is an object of the present invention to provide a device for scanning the surface of a data recording medium, to more rapidly locate surface discontinuities and more accurately characterize a profile of each discontinuity.

Another object is to provide a method for scanning data storage media for surface flaws and other discontinuities in a non-contact, non-destructive manner usable at various stages of media fabrication.

A further object is to provide a surface scanning process and device employing a more selective approach to data acquisition, to more accurately characterize the profiles of surface discontinuities while avoiding unduly burdensome data storage requirements.

Yet another object is to provide a device using coherent energy in a non-contact scanning of the surface of a data recording medium, to more effectively optimize focusing of the coherent energy during scanning.

SUMMARY OF THE INVENTION

To achieve these and other objects, there is provided a device for detecting local surface discontinuities in a data storage medium. The device includes a storage media support stage maintaining a data storage medium in a selected orientation such that a substantially planar selected surface of the data storage medium is substantially in a selected plane. A coherent energy source is provided for generating a linearly propagating object beam of the coherent energy. A beam guide is adapted to direct the object beam along an optical path onto the selected surface in an axial direction substantially normal to the selected plane. The beam guide further is adapted to collect a portion of the coherent energy reflected away from the selected surface, and to direct the collected coherent energy further along the optical path to a predetermined destination.

The device further includes a translating stage adapted to cause a controlled movement of the data storage medium and a portion of the beam guide relative to one another to cause the object beam to trace a scanning path over the selected surface. Discontinuities in the selected surface, when traversed by the object beam as it traces the scanning path, reflect the portion of the coherent energy from different axial locations to cause corresponding changes in an optical path length of the optical path. A sensing apparatus, disposed proximate the predetermined destination, is adapted to detect the changes in the optical path length.

Preferably, the changes in the optical path length are measured interferometrically. This is advantageously accomplished by generating a reference beam of the coherent energy and causing the reference beam to interfere with the object beam at the predetermined destination. Changes in the optical path length vary the interference to change the intensity of coherent energy at the predetermined destination. Precise measurements of discontinuities, as to non-planar deviations in the nanometer and subnanometer ranges, are enabled because the intensity is highly sensitive to changes in the optical path length.

Typically the data storage media are magnetic disks, in which case the support stage and translating stage include a rotatable spindle and a carrier for translating the beam guide portion radially relative to the spindle. Rotation and translation can occur in concert, causing the laser to scan a spiral path over the disk surface.

Preferably, discontinuities are sensed only when changes in the optical path length exceed a predetermined threshold, e.g. 10–50 nm. The optical path length can be sampled at a high rate, typically 50,000,000 samples per second, which allows accurate profiling of discontinuities during disk rotation at speeds in the range of 10–200 revolutions per second. Each revolution can trigger an index pulse, whereupon the timing of discontinuity registration pulses relative to the index pulses can be used to locate the discontinuities on the disk surface. If desired, a record of the discontinuity locations is created and later used to guide an optical microscope or other inspection device to the discontinuities.

Interferometric measurements are enhanced when the object beam is, to the extent possible, focused at the surface of the data storage medium during scanning. To this end, a further aspect of the invention involves repeatedly scanning a segment of the scanning path while generating an intensity value indicating the intensity corresponding to scanning that segment, while a focusing lens along the optical path is stepped in several different axial locations. The resulting set of intensity values are stored in a memory, with the highest or maximum intensity value indicating the optimally focused lens location. If desired, the lens may be tested from time to time and repositioned if necessary during a given scan.

The device is advantageously used in a process for detecting and observing surface discontinuities in a data storage medium, including the following steps:

a. while maintaining a data storage medium in a selected orientation to position a substantially planar selected surface thereof substantially in a selected plane, guiding a coherent energy object beam along an optical path toward the selected surface and causing the object beam to trace a scanning path over the selected surface;

b. collecting a portion of the coherent energy reflected away from the selected surface, and further guiding the collected coherent energy along the optical path to a predetermined destination; and c. interferometrically sensing any changes in an optical path length of the optical path, and generating a registration signal responsive to sensing a change in the optical path length that exceeds a predetermined threshold, thereby to indicate a discontinuity.

Thus in accordance with the present invention, data storage media may be inspected interferometrically, in a non-destructive, non-contact manner resulting in a record of the locations of surface discontinuities, and profile information about each discontinuity. A storage medium can be inspected at different stages of its fabrication, from the initial formation of the substrate, through the application of any one of several magnetic thin film layers onto the substrate. This facilitates inspection of the substrate per se, and identification of a particular layer giving rise to interruptions in surface planarity. The threshold for sensing discontinuities can be set to ensure that data are collected and retained only when a discontinuity of a predetermined size is encountered, which dramatically reduces the memory needed for storing profile information, a particularly useful feature in view of the high sampling rates involved.

IN THE DRAWINGS

For a further appreciation of the above and other advantages, reference is made to the following detailed description and to the drawings, in which.

DETAILED DESCRIPTION OF THE PREFERRED EMBODIMENTS

Figure 1:
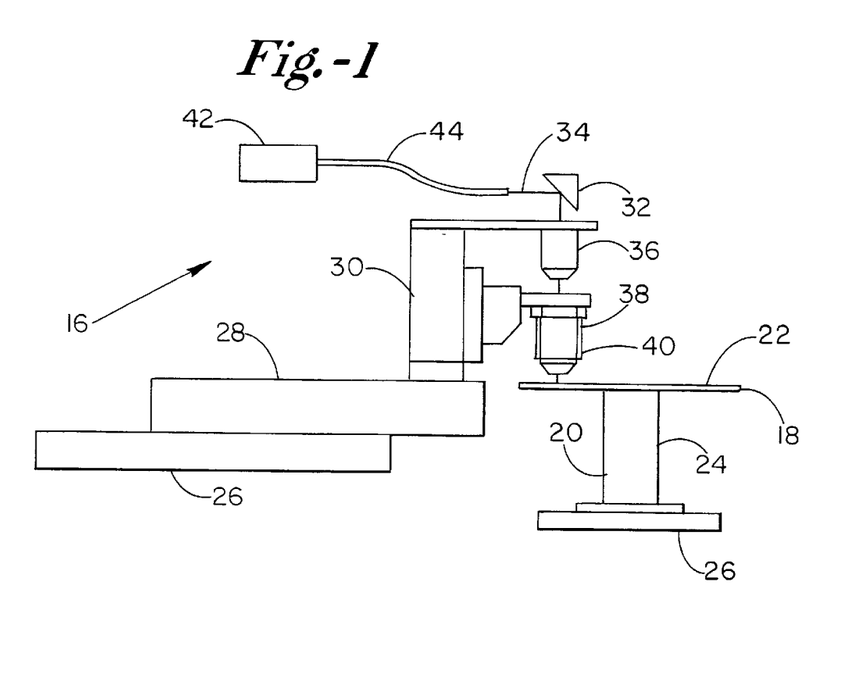
FIG. 1 is a schematic elevation of a system for interferometrically inspecting data storage media.
Figure 2:
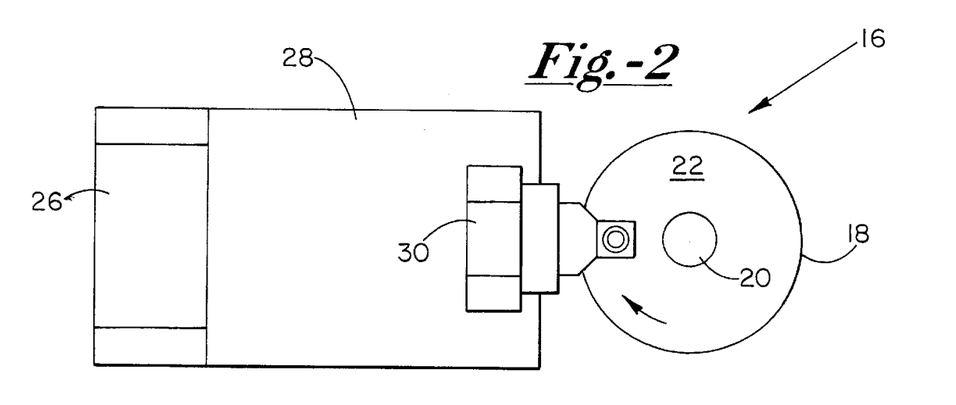
FIG. 2 is a schematic top plan view of the system.

Turning now to the drawings, there is shown in FIGS. 1 and 2 a laser scanning system 16 for use in a non-destructive, non-contact inspection of data storage media, particularly magnetic disks, for surface defects. Components of the system are used to generate a laser beam, move a magnetic disk and the laser beam relative to each other so that the beam scans a surface of a disk, and sense changes in the laser beam as it traces the scanning path to generate information about the surface.

More particularly, a magnetic disk 18 is supported on a precision air bearing spindle 20, for rotation about a vertical spindle axis at velocities ranging from about 10 to about 200 revolutions per second. Disk 18 is maintained in a horizontal orientation as shown in FIG. 1, i.e. with a substantially planar top surface 22 of the disk in a horizontal plane. A spindle shaft 24 of the spindle is mounted to a stationary deck 26 through bearings and incorporates a motor including stator windings and a rotor (not shown) in a known manner to control shaft and disk rotation. Also mounted to deck 26 is a linear slide or carriage 28. An optics assembly 30 is supported on the slide, for reciprocal movement with the slide radially with respect to the disk and spindle, i.e. to the left and right as viewed in FIGS. 1 and 2. The optics assembly includes several optical components: an optical mirror 32 for directing an object beam 34 downwardly (as viewed in FIG. 1) toward surface 22; and beam shaping optics including a collimating lens 36 and a focusing lens 38. Focusing lens 38 is supported on a piezoelectric element 40 for axial movement, i.e. vertical travel as viewed in FIG. 1. While lens 38 and element 40 are not shown in detail, a voltage level applied to the piezoelectric element is varied in a known manner to adjust the lens axial position.

Object beam 34 is provided by an interferometer 42 and transmitted by a fiber optic cable 44 to optics assembly 30 near mirror 32, so that laser energy exiting the fiber optic cable is reflected by the mirror downward as previously noted.

Focusing lens 38 is axially positioned to focus object beam 34 onto surface 22 of the disk. Focusing the beam enhances the intensity of light scattered by surface 22. A portion of the laser energy is reflected axially, i.e. upwardly as viewed in FIG. 1, where it is collected by focusing lens 38 and transmitted through collimating lens 36 to mirror 32, then back to interferometer 42 via the fiber optic cable. Thus, an optical path of the laser energy is not limited to that portion from the interferometer toward surface 22, but further encompasses return travel of a collected portion of the scattered energy.

Figure 3:
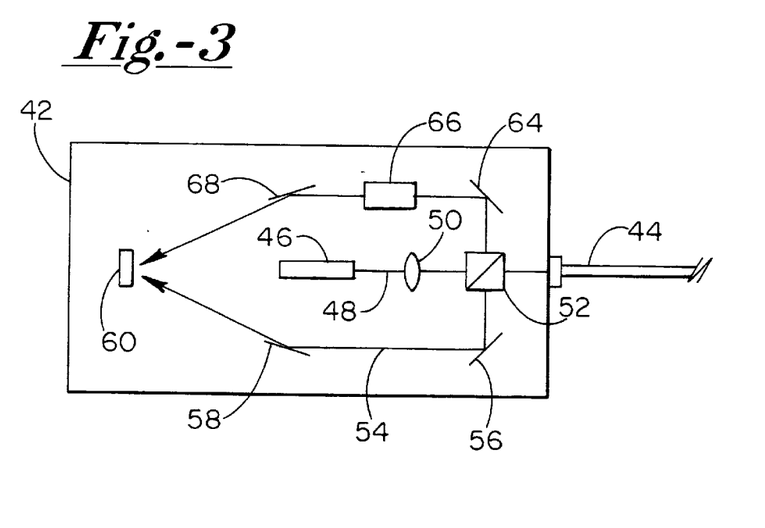
FIG. 3 is a more detailed schematic view of an interferometer of the system.

As seen in FIG. 3, interferometer 42 includes a laser 46 (HeNe) that generates a laser beam 48. Beam 48 diverges as it proceeds toward a collimating lens 50. From lens 50, the laser beam proceeds to a beam splitting prism 52. Beyond prism 52, a portion of the laser beam proceeds to fiber optic cable 44 for transmission as object beam 34.

Another portion of the beam is reflected by prism 52 to provide a reference beam 54. A mirror 56 reflects the diverted collimated reference beam toward another mirror 58, which in turn reflects reference beam 54 toward a photosensor 60 which acts as a light collecting element 60. The photosensor detects laser energy from interference beams 34 and 54 measure the intensity of the energy at the photosensor.

The portion of the scattered energy returning to interferometer 42 via the fiber optic cable also encounters beam splitting prism 52. Part of this beam, which can be thought of as a returned portion of object beam 34, is directed upwardly out of prism 52, reflected by a mirror 64 through a Bragg cell or other frequency modulating device 66, then reflected by a mirror 68 toward photosensor 60. Thus, the entire optical path length of object beam 34 includes the diverted portion of the returned beam that passes through Bragg cell 66 and is reflected onto photosensor 60, which can be thought of as a destination for the object beam.

As object beam 34 and reference beam 54 reach photosensor 60, the beams interfere with one another. The interference region is stable, so long as the positions of beams 34 and 54 remain stable. However, any change in the optical path length phase shifts object beam 34 with respect to reference beam 54, altering the intensity at photosensor 60. Photosensor 60 responds to the changes in intensity, to register changes in the optical path length.

Figure 4:
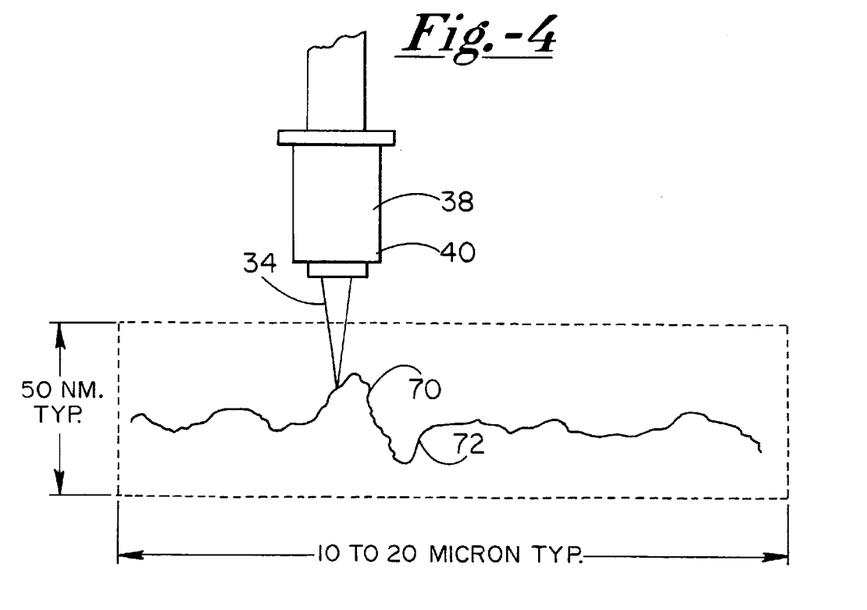
FIG. 4 is a more detailed view of a portion of the system, illustrating a laser beam directed onto a surface under inspection.

System 16 employs object beam 34 to detect and measure surface discontinuities, i.e. non-planarities or faults, in surface 22. While disk 18 is rotated by spindle 20, the focused object beam is moved radially by linear slide 28, thus causing the object beam to trace a spiral scanning path over the disk surface. A segment of surface 22, in particular a segment of the scanning path, is shown greatly magnified in FIG. 4, to reveal a surface roughness including a peak 70 above the surface plane and the depression 72 below the surface plane, along with other less prominent peaks and depressions. As seen from this figure, the axial (vertical) distance between lens 38 and surface 22 increases as the beam encounters depressions, and is reduced as the beam encounters peaks. In short, the optical path length is a function of the local surface topography from which the laser beam is reflected. Changes in the optical path length represent phase shifts in object beam 34 (particularly the returned portion) relative to reference beam 54. Such shifts alter the interference intensity, causing fluctuations in the intensity of laser energy at photosensor 60. Photosensor 62 generates an analog electrical signal, the voltage of which varies with changes in the optical path length, thus to represent surface discontinuities encountered along the scanning path.

Figure 5:
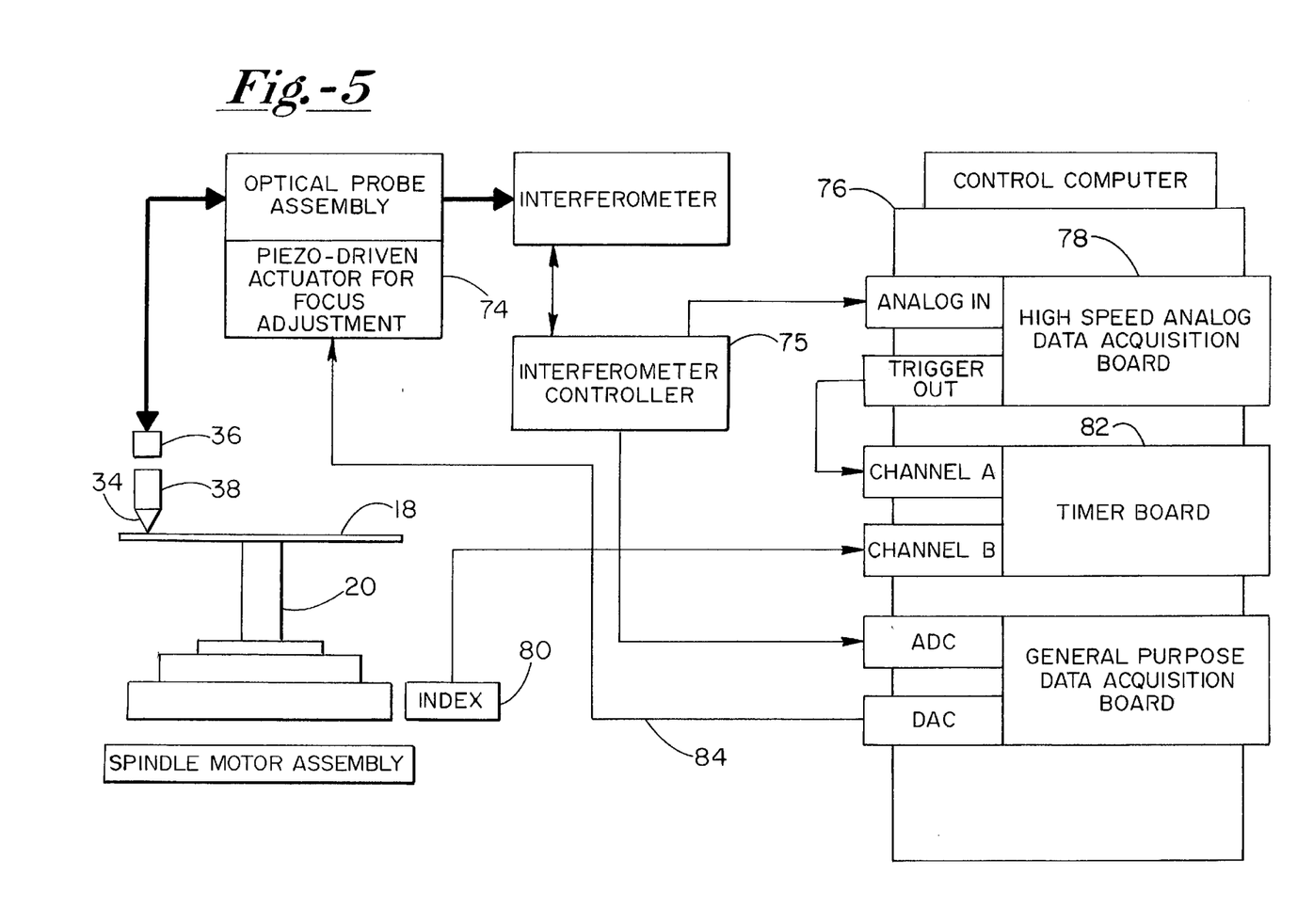
FIG. 5 is a schematic view of certain signal processing architecture of the system.

Operation of the system can be considered in connection with FIG. 5, showing magnetic disk 18 on spindle 20, and optics assembly 30 positioned above the disk to provide object beam 34. The optics assembly includes an actuator 74 for applying selected voltages to the piezoelectric element, to adjust the position of lens 38 for focusing the object beam. As the return portion of object beam 34 is provided to interferometer 42, an interferometer controller 75 provides the analog electrical output of photosensor 62 to a processor 76, more particularly to a high speed analog data acquisition circuit 78 via an A/D (analog to digital) converter, not shown.

While detecting surface discontinuities or flaws is essential, there is no need to retain data reflecting the absence of flaws (i.e. sufficient planarity) in surface 22. Accordingly, the memory required to store surface information is considerably reduced, limited to information locating or characterizing non-planarities. To this end, processor 76 includes a threshold setting component in its data acquisition circuitry, for generating a trigger or registration pulse only when the analog electrical signal from photosensor 62 exceeds a predetermined threshold, exhibiting a change in the optical path length that exceeds a predetermined displacement threshold, e.g. in the range of 10–50 nm in conjunction with a typical transducing head glide height of 25 nm. If desired, the predetermined threshold can be direction sensitive, e.g. setting a 25 nm threshold for peaks and a 38 nm threshold for depressions. This requires use of Bragg cell 66 to frequency shift the object beam as noted above (or alternatively to shift the reference beam), to enable the sensing of the direction of a change in the optical path length, as opposed to sensing merely the magnitude of the change.

In any event, circuitry within processor 76 generates a registration pulse to trigger a capturing of the data within a predetermined window that begins with the registration pulse. The window is a time interval, but also can be thought of as a distance along the arcuate scanning path, given the relative motion of the disk and object beam. The appropriate window size depends on a variety of factors including the size of the disk, the disk rotational speed during testing, and the anticipated defect size, particularly a maximum expected size. As one example, for an arcuate segment of the scanning path with a radius of approximately 6 cm, each disk revolution involves arcuate travel of about 20 cm, whereupon a speed of 50 revolutions per second yields a linear tangential speed of about 10 meters per second. Given this speed, a window timed at 2 microseconds is equivalent to arcuate travel of about 20 microns. A sampling rate of 50,000 samples per second, throughout the 2 microsecond window, yields 100 samples of the analog electrical signal. If disk 18 is to be rotated at the same angular speed throughout the test, a window size selection must take into account the increasing tangential speed with increasing radius. If a more accurate surface profile is desired, the number of samples during the window is increased, either by increasing the sampling rate or reducing the disk rotational speed. The sampling rate can be increased to about 100,000,000 samples per second. Other applications may call for larger windows, e.g. up to about 200 microns.

Object beam 34 is used both to locate discontinuities, and to characterize the topography of each discontinuity. Mapping the location of each discontinuity involves generating index or timing pulses, one for each revolution of the disk, at the same angular location on the disk. With beam 34 moved radially in conjunction with disk rotation as described, a count of the index pulses can be used to determine the radial location of the beam. Further, the angular location of a particular flaw, as evidenced by its associated registration pulse, can be determined based on the temporal spacing between the registration pulse and one of the adjacent index pulses.

Accordingly an index sensor 80 (FIG. 5) provides a timing pulse to a timing circuit 82 within processor 76. When object beam 34 encounters a discontinuity during its scan, the resulting registration or triggering pulse is provided to the timing circuit, thus to record a temporal spacing between the registration pulse and the preceding index pulse. Given that the size of the disk is known and its rotational speed is controlled, the temporal spacing and index pulse count cooperate to pinpoint the location of the discontinuity on the disk surface, providing an address stored in terms of cylindrical coordinates, i.e. radius and angle.

Characterization of each discontinuity can occur at several levels. At a minimum, the registration pulse alone indicates a certain minimum height or depth of the discontinuity. Further characterizing information can be stored with respect to each flaw, e.g. a record of the maximum sampled height and maximum sampled depth; or, the entire set of samples to yield a digital profile representation or topography signature that closely corresponds to the sampled analog electrical signal. Processor 76 includes memory registers for storing the detected flaws, each identified by a unique address in association with the topography characterizing information.

The interferometric sensing and characterization of discontinuities is more effective when the returned object beam has a higher amplitude. To this end, the object beam to the extent possible should be precisely focused at surface 22. A precise focus results from a correct longitudinal spacing of focusing lens 38 with respect to collimating lens 36 and the disk surface. It is undesirable to fix the focusing lens axial position, for several reasons. One is a natural variance in thickness among magnetic disks or disk substrates. A set of substrates for which a nominal thickness is 31.5 mils may include disks of 31 mil thickness or 32 mil thickness, for example. Secondly, testing the same disk at different processing stages (e.g. substrate, substrate+underlayer, substrate+underlayer+magnetizable recording layer, etc.) requires focusing adjustment. Further, there is a tendency in particularly thin disks to droop when supported on spindle 20, causing a deviation of perhaps 5–6 microns from absolute surface planarity.

To compensate for these variations, focusing lens 38 is mounted on piezoelectric element 40 for axial movement as discussed above. With further reference to FIG. 5, interferometer controller 75 provides a signal, based on intensity at collecting element 60, to processor 76. In turn, a level of voltage applied to the piezoelectric element is controlled by circuitry in processor 76 and provided via a line 84.

This control and feedback are used in concert to determine an optimum axial position for lens 38 corresponding to the desired focus. In particular, focusing lens 38 is adjustable over a range of axial positions. This permits processor 76 to step lens 38 sequentially through several axial positions along the range. In connection with each position, spindle 20 rotates the disk so that object beam 34 scans a selected arcuate segment of the scanning path, e.g. one revolution at a selected radius. Beam 34 is caused to scan the same selected segment at each lens position, preferably in accordance with a program stored in processor 76, although the sequence could be performed manually. An amplitude or intensity value is stored in connection with each such scan. After all scans, the scan with the maximum amplitude, i.e. reflecting the maximum intensity of the laser energy at collecting element 60, is selected as the optimum focusing distance.

If desired, the preceding test can be performed at several different stages of a surface scan, e.g. at regular radially spaced apart intervals, either to confirm a correct lens adjustment or to enable an axial lens adjustment to re-establish the desired focus.

Figure 6:
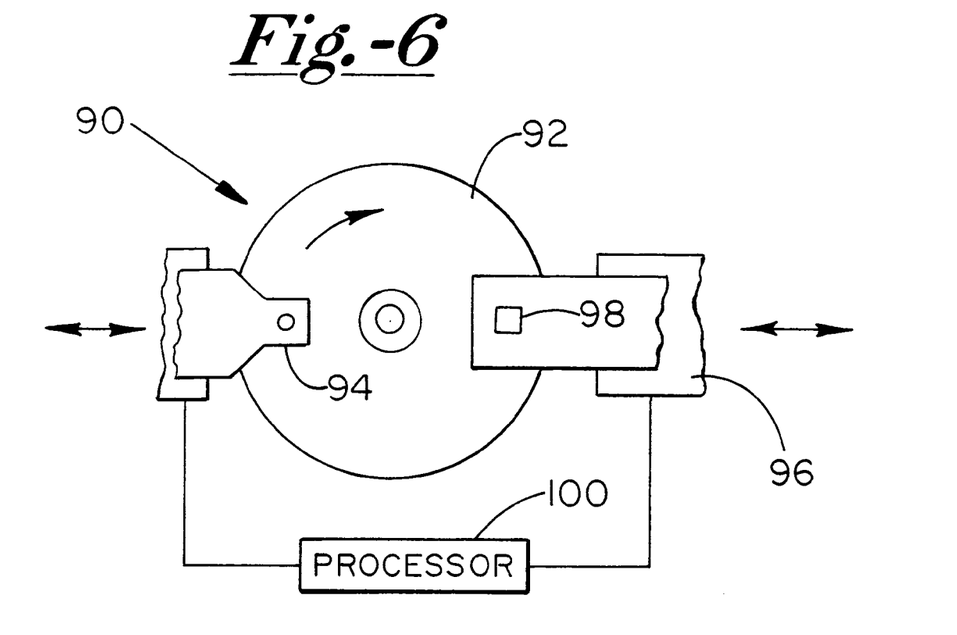
FIG. 6 is a schematic view of an alternative system for inspection according to the present invention.

FIG. 6 illustrates an alternative system 90 incorporating a spindle mounted magnetic disk 92 and laser beam generating and guiding optics 94 similar to those previously described, further incorporating a linear slide or carriage 96 supporting an optical microscope 98 for radial movement relative to magnetic disk 92. A computer 100, coupled to optics assembly 94 and to a spindle supporting the disk in the manner previously described, also is coupled to carriage 96 to control movement and positioning of the optical microscope. System 90 initially is used in a manner similar to system 16 to detect discontinuities and to map respective discontinuity locations. Only minimal topography characterizing information is required.

Following mapping, carriage 96 and the spindle are controlled in accordance with the recorded flaw location information, to position microscope 98 successively at each of the previously detected flaws. According to one preferred approach, carriage 96 is moved radially as the disk is rotated, to cause microscope 98 to track the scanning path previously traced by the object beam, so that the microscope encounters the discontinuities in the same sequence as they were detected.

Figure 7:
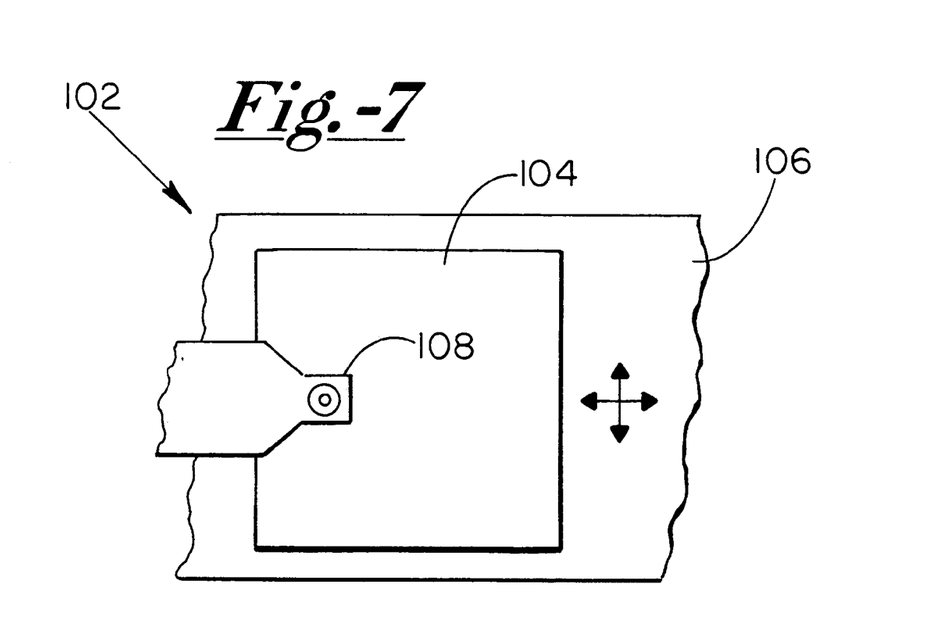
FIG. 7 is a schematic view of another alternative embodiment inspection system according to the invention.

FIG. 7 illustrates a further embodiment system 102 in which a rectangular data storage device 104 is supported on a translation stage 106, controllable to move storage device 104 in a series horizontal (as viewed in the figure) sweeps, in a stepped sequence that positions each sweep adjacent and spaced slightly vertically from its preceding sweep. In this system, an optics assembly 108 is maintained stationary. Suitable alternatives to this system involve applying a similar stepped sequence to the optics assembly while maintaining the data storage device stationary, and reciprocating the data storage device while advancing the optics assembly in steps accompanying the reciprocations.

Thus in accordance with the present invention, surface defects in data storage media are detected and characterized in a non-destructive, non-contact interferometric mode. Testing can occur at any stage of media fabrication, to characterize a disk substrate, a completed medium incorporating all of the thin film layers normally applied to the substrate, or at any intermediate stage. Interferometric detection is highly sensitive to minute phase shifts in the beam, which enables detection of flaws in the nanometer range. A detection threshold limits stored data to that which is pertinent to detected flaws. The data can simply identify the location of a flaw, or may also characterize a topography of the flaw. If desired, the discontinuity location data may be used to position an optical microscope or other inspection device adjacent various detected flaws.

What is claimed is:

1. A device for detecting local surface discontinuities in a generally planar surface of a data storage device, including:

a storage media support stage maintaining a data storage device in a selected orientation such that a substantially planar selected surface of the data storage device lies substantially in a selected plane;

a coherent energy source for generating an object beam of the coherent energy;

a beam guide adapted to direct the object beam along an optical path toward the selected surface in an axial direction substantially normal to the selected plane, said beam guide further being adapted to collect a portion of the coherent energy reflected away from the selected surface in said axial direction, and to direct the collected coherent energy further along the optical path to a predetermined destination;

a translating stage adapted to cause a controlled movement of the data storage device and a portion of the beam guide relative to one another, to cause the object beam to trace a scanning path over the selected surface;

wherein non-planar discontinuities in the selected surface, when traversed by the object beam as it traces the scanning path, reflect said portion of the coherent energy from different axial locations to cause corresponding changes in an optical path length of the optical path; and a sensing apparatus disposed proximate said predetermined destination, adapted to detect said changes in the optical path length.

2. The device of claim 1 wherein:

said sensing apparatus includes means for generating a reference beam of the coherent energy and causing the reference beam to interfere with the object beam at said predetermined destination to produce an intensity that changes with said changes in the optical path length, thereby to vary an intensity of the coherent energy at the predetermined destination responsive to said changes in said optical path length; and said sensing apparatus further includes a coherent energy detector adapted to generate an analog electrical signal having a signal level that varies with changes in said intensity.

3. The device of claim 2 further including:

a processing means coupled to receive said analog electrical signal input, for generating a registration pulse to indicate a traversal of a discontinuity by the object beam whenever a variation in the signal level exceeds a predetermined threshold.

4. The device of claim 3 wherein:

the processing means includes a means for converting the analog electrical signal into a digital profile representation of each detected discontinuity, and a memory for storing the digital profile representations.

5. The device of claim 4 wherein:

each of the digital profile representations consists of a predetermined number of regularly temporally spaced samples of the analog electrical signal, and thus encompasses a predetermined time interval beginning with its associated registration pulse.

6. The device of claim 4 wherein:

the processing means further includes a means for generating an address associated with each of the detected discontinuities to indicate a location of the associated discontinuity on the selected surface, and said memory stores the addresses.

7. The device of claim 6 wherein:

the means for generating addresses includes a means for generating index pulses at predetermined intervals along said scanning path, and means for determining a spacing between each of the registration pulses and one of the index pulses.

8. The device of claim 6 further including:

an optical inspection device, a support stage for supporting the optical inspection device in spaced apart relation to the data storage device for movement over the selected surface in directions parallel to the selected plane, and a control means, coupled to the memory, for positioning the optical inspection device proximate a selected discontinuity based an address of the selected discontinuity stored in the memory.

9. The device of claim 2 further including:

a modulation means for shifting the frequency of one of said object beam and reference beam, by a predetermined amount.

10. The device of claim 1 wherein:

said beam guide includes a focusing lens disposed along the optical path and near the selected surface, movable in the axial direction to focus the beam substantially at the selected surface.

11. The device of claim 10 further including:

a means for sensing an intensity of the coherent energy at said destination and generating a lens control signal that varies with said intensity, and a lens position controller for axially positioning the focusing lens responsive to the control signal.

12. The device of claim 1 wherein:

the data storage device is a disk, the media support stage includes a spindle rotatable about an axis normal to the selected plane, and the translating stage includes a means for rotating the spindle and a means for translating said portion of the beam guide radially relative to the spindle.

13. The device of claim 12 wherein:

the spindle rotating means and beam guide translating means are operable in concert, whereby said scanning path is a spiral.

14. The device of claim 2 wherein:

the coherent energy source comprises a laser generating the coherent energy as a laser beam, and beam splitting optics positioned to receive the laser beam and generate the object beam and the reference beam based on the laser beam.

15. An apparatus for scanning a surface of a data storage device, including:

a storage media support stage for maintaining a data storage device in a selected orientation with a substantially planar selected surface of the data storage device substantially parallel to a selected plane;

a coherent energy source for generating a linearly propagating object beam of the coherent energy;

a beam guide adapted to direct the object beam along an optical path onto the selected surface in an axial direction substantially normal to the selected plane, said beam guide further being adapted to collect a portion of the coherent energy reflected away from the selected surface in said axial direction and direct the collected coherent energy further along the optical path to a predetermined destination, said beam guide including a focusing lens disposed along the optical path near the selected surface and movable in the axial direction;

a translating stage adapted to controllably move the data storage device and a portion of the beam guide including the focusing lens relative to one another in directions substantially parallel to the selected plane, to cause the object beam to trace a scanning path over the selected surface;

a coherent energy detector for sensing an intensity of the coherent energy at the predetermined destination while the object beam traces a segment of the scanning path, and generating an intensity value indicating the intensity corresponding to scanning said segment;

a lens positioning stage operably coupled to the focusing lens to move the lens axially within a predetermined range and to alternatively place the lens at a plurality of different lens locations within said range; and a processor coupled to the detector and to the lens positioning stage, including a memory for storing a plurality of the intensity values, each corresponding to said scanning said segment at a different one of the lens locations.

16. The apparatus of claim 15 wherein:

said processor further includes a means for selecting one of the lens locations as an optimally focused location based on its association with a maximum one of the intensity values stored in said memory.

17. The apparatus of claim 16 wherein:

said processor further is adapted to provide a control signal to the lens positioning stage, to cause the lens positioning stage to place the focusing lens at the selected lens location.

18. The apparatus of claim 15 wherein:

the data storage device is a disk, the media support stage includes a spindle rotatable about an axis normal to the selected plane, the translating stage includes a means for rotating the spindle and a means for translating said portion of the beam guide radially relative to the spindle, and said selected segment of the scanning path is defined by a single, complete rotation of the spindle.

19. The apparatus of claim 15 wherein:

said lens positioning stage includes a piezoelectric element supporting the focusing lens, and a means for selectively altering a voltage input to the piezoelectric element to determine the lens location.

20. The apparatus of claim 15 further including:

a means for generating a reference beam of the coherent energy and causing the reference beam to interfere with the object beam at said predetermined destination, to enable an interferometric detection of any changes in a length of said optical path as the object beam traces the scanning path.

21. A device for detecting and observing local surface discontinuities in a substantially planar surface of a data storage medium, including:

a storage media support stage for maintaining a data storage device in a selected orientation with a substantially planar selected surface of the data storage device substantially parallel to a selected plane;

a coherent energy source for generating an object beam and a reference beam of the coherent energy;

a first beam guide adapted to direct the object beam along an optical path toward the selected surface in an axial direction substantially normal to the selected plane, said first beam guide further being adapted to collect a portion of the coherent energy reflected away from the selected surface and to direct the collected coherent energy further along the optical path to a predetermined destination;

a translating stage adapted to controllably move the data storage device and a portion of the beam guide relative to one another, to cause the object beam to trace a scanning path over the selected surface;

a second beam guide for directing the reference beam to interfere with the object beam at the predetermined destination, to enable an interferometric detection of a surface discontinuity in the selected surface that, as it is traversed by the object beam tracing the scanning path, changes an optical path length of the optical path by more than a predetermined amount;

a sensor near the predetermined destination, and means coupled to the sensor adapted to generate a registration pulse responsive to said detection of a discontinuity;

a processor adapted to receive the registration pulse and to generate an address based on when the registration pulse is generated, said processor including a memory for storing a plurality of addresses each uniquely associated with one of a plurality of detected discontinuities; and an optical inspection device supported in axially spaced apart relation to the selected surface, movable relative to the selected surface in directions parallel to the selected plane, and positionable adjacent a selected discontinuity, based on the address in said memory associated with the selected discontinuity.

22. The device of claim 21 wherein:

the optical inspection device is movable relative to the data storage device, through control of said translating stage.

23. The device of claim 21 wherein:

said sensor further generates an analog electrical signal representing a profile of the detected discontinuity, and the memory further stores a plurality of profiles, each associated with a different one of the detected discontinuities.

24. The device of claim 21 wherein:

the processor includes a means for generating index pulses at predetermined intervals along the scanning path, and means for measuring a spacing between each of the registration pulses and one of the index pulses.

25. A process for detecting surface discontinuities in a substantially planar surface of a data storage device, including:

supporting a data storage device in a selected orientation with a substantially planar selected surface of the data storage device parallel to a selected plane;

guiding a coherent energy object beam along an optical path to direct the object beam toward the selected surface in an axial direction substantially normal to the selected plane, then collecting a portion of the coherent energy reflected away from the selected surface and directing the collected coherent energy further along the optical path to a predetermined destination;

while so guiding the object beam, causing the object beam to trace a scanning path over the selected surface;

monitoring the optical path for any changes in an optical path length thereof, and generating a registration signal responsive to sensing a change in the optical path length that exceeds a predetermined threshold.

26. The process of claim 25 wherein:

said monitoring includes causing a reference beam of the coherent energy to interfere with the object beam at the predetermined destination, thus to interferometrically detect the changes in the optical path length.

27. The process of claim 25 wherein:

said monitoring further includes generating a registration pulse responsive to detecting a change in the optical path length greater than the predetermined threshold.

28. The process of claim 27 wherein:

said monitoring further includes generating an analog electrical signal representative of a profile of the sensed discontinuity.

29. The process of claim 27 further including:

generating a plurality of index pulses at predetermined time intervals while causing the object beam to trace the scanning path, and determining a spacing between each of the registration pulses and one of the index pulses to locate the sensed discontinuity.

30. The process of claim 26 further including:

frequency shifting one of the object beam and reference beam by a predetermined amount.

31. The process of claim 25 wherein:

the controlled movement of the data storage device and the object beam relative to one another includes rotating the data storage device while translating the object beam radially thereof, to define a spiral scanning path.

32. A process for detecting and observing surface discontinuities in a substantially planar surface of a data storage medium, including:

while maintaining a data storage medium in a selected orientation to position a substantially planar selected surface thereof substantially in a selected plane, guiding a coherent energy object beam along an optical path toward the selected surface and causing the object beam to trace a scanning path over the selected surface;

collecting a portion of the coherent energy reflected away from the selected surface, and further guiding the collected coherent energy along the optical path to a predetermined destination;

interferometrically sensing any changes in an optical path length of said optical path, and generating a registration signal responsive to sensing a change in the optical path length that exceeds a predetermined threshold, thereby to indicate a discontinuity.

33. The process of claim 32 further including:

generating an address uniquely associated with the sensing of each discontinuity to identify a unique location of the discontinuity on the selected surface, supporting an optical inspection device in axially spaced apart relation to the selected surface for movement relative to the selected surface in directions parallel to the selected plane, and controlling movement of the optical inspection device according to said address to position the optical inspection device adjacent the detected discontinuity.

34. An apparatus for detecting surface discontinuities in a substantially planar surface of a data storage medium, including:

means for maintaining a data storage medium in a selected orientation to position a substantially planar selected surface thereof substantially in a selected plane;

means for guiding a coherent energy object beam along an optical path toward the selected surface and causing the object beam to trace a scanning path over the selected surface;

means for collecting a portion of the coherent energy reflected away from the selected surface, and further guiding the collected coherent energy along the optical path to a predetermined destination;

means for sensing any changes in an optical path length of said optical path; and means for generating a registration signal responsive to sensing a change in the optical path length that exceeds a predetermined threshold, thereby to indicate the presence of a surface discontinuity along the scanning path.

* * * * *